United States Patent
Romes et al.

(10) Patent No.: US 7,748,197 B2
(45) Date of Patent: Jul. 6, 2010

(54) METHOD AND/OR SYSTEM FOR COMPENSATING FOR EFFECTS OF HEAT FLOW AND/OR AIR FLOW THROUGH FIBERGLASS INSULATION

(75) Inventors: Gary E. Romes, Cincinnati, OH (US); David W. Yarbrough, Cookeville, TN (US)

(73) Assignee: Guardian Building Products, Inc., Greer, SC (US)

( * ) Notice: Subject to any disclaimer, the term of this patent is extended or adjusted under 35 U.S.C. 154(b) by 909 days.

(21) Appl. No.: 11/327,648

(22) Filed: Jan. 9, 2006

(65) Prior Publication Data
US 2006/0272280 A1 Dec. 7, 2006

Related U.S. Application Data

(63) Continuation-in-part of application No. 11/127,316, filed on May 12, 2005, now Pat. No. 7,226,206.

(51) Int. Cl.
*E04C 2/34* (2006.01)
*E04B 1/00* (2006.01)
*E04B 1/74* (2006.01)
*G01K 17/00* (2006.01)
*G01K 1/16* (2006.01)

(52) U.S. Cl. .................. 52/794.1; 52/745.09; 52/404.1; 52/404.3; 374/29; 374/135

(58) Field of Classification Search ................ 52/404.1, 52/406.1, 407.3, 404.3, 742.1, 742.13, 745.09; 374/29; 156/71
See application file for complete search history.

(56) References Cited

U.S. PATENT DOCUMENTS

| | | | | |
|---|---|---|---|---|
| 3,269,185 A | * | 8/1966 | Francisco | .................... 374/19 |
| 4,071,984 A | * | 2/1978 | Larrow | ........................ 52/79.1 |
| 4,155,244 A | | 5/1979 | Bhattacharyya | |
| 4,534,663 A | * | 8/1985 | Poppendiek et al. | .......... 374/43 |
| 4,839,222 A | * | 6/1989 | Jain | ............................ 442/375 |
| 5,160,465 A | | 11/1992 | Soderberg | |
| 5,389,167 A | * | 2/1995 | Sperber | ....................... 156/71 |

(Continued)

OTHER PUBLICATIONS

"Dynamic Insulation a Theoretical Analysis of Thermal Insulation Through Which a Gas or Fluid Flows", Anderlind et al., Swedish Council for Building Research, Document D8:1983.

*Primary Examiner*—Brian E Glessner
*Assistant Examiner*—Omar Hijaz
(74) *Attorney, Agent, or Firm*—Dority & Manning, P.A.

(57) ABSTRACT

A method and/or system is provided that compensates for the flow of air through fiberglass insulation. In certain example embodiments, a dynamic heat flow meter or the like is provided for measuring and/or determining any detrimental effects of air flow through insulation such as fiberglass insulation. Once the possible detrimental effects are recognized, an insulation system is adapted (e.g., by providing a foam based insulation in a wall cavity in addition to the fiberglass insulation) to compensate, or substantially compensate, for the effects of air flow through the fiberglass. For instance, a sufficient amount of foam insulation may be provided in a cavity adjacent fiberglass, where the foam blocks or substantially blocks air from flowing through the cavity, thereby compensating for the effects of air flow through fiberglass and permitting the intended R-value to be maintained or substantially maintained.

12 Claims, 4 Drawing Sheets

U.S. PATENT DOCUMENTS

| | | | |
|---|---|---|---|
| 5,410,448 A * | 4/1995 | Barker et al. | 361/695 |
| 5,641,368 A | 6/1997 | Romes et al. | |
| 5,667,301 A * | 9/1997 | Jurkowski et al. | 374/43 |
| 5,702,185 A * | 12/1997 | Heikal | 374/29 |
| 5,733,624 A | 3/1998 | Syme et al. | |
| 5,746,854 A | 5/1998 | Romes et al. | |
| 5,879,615 A | 3/1999 | Syme et al. | |
| 5,921,055 A | 7/1999 | Romes et al. | |
| 5,940,784 A | 8/1999 | El-Husayni | |
| 5,952,418 A | 9/1999 | Romes et al. | |
| 6,135,747 A | 10/2000 | Syme et al. | |
| 6,334,228 B1 * | 1/2002 | Schmid | 5/726 |
| 6,487,866 B1 * | 12/2002 | Fesmire et al. | 62/51.1 |
| 6,967,051 B1 | 11/2005 | Augustynowicz et al. | |
| 6,991,366 B2 * | 1/2006 | Naka et al. | 374/44 |
| 2003/0061777 A1 * | 4/2003 | Alderman | 52/407.3 |

* cited by examiner

METHOD AND/OR SYSTEM FOR COMPENSATING FOR EFFECTS OF HEAT FLOW AND/OR AIR FLOW THROUGH FIBERGLASS INSULATION

This application is a continuation-in-part (CIP) of U.S. Ser. No. 11/127,316, filed May 12, 2005, now U.S. Pat. No. 7,226,206 the entire disclosure of which is hereby incorporated herein by reference.

This application relates to a method and/or system that compensates for the flow of air through fiberglass insulation. In certain example embodiments, dynamic heat flow meter or the like is provided for measuring the thermal properties of a material (e.g., insulation such as fiberglass inclusive insulation, or any other suitable material) including any detrimental effects of air flow therethrough. Once the possible detrimental effects are recognized, the insulation system is adapted (e.g., by providing a foam based insulation in a wall cavity in addition to the fiberglass insulation) to compensate, or substantially compensate, for the effects of air flow through the fiberglass. For instance, a sufficient amount of foam insulation may be provided in the cavity adjacent the fiberglass insulation, where the foam can block or substantially block the air flow through the cavity, thereby compensating for the effects of air flow through fiberglass and permitting the intended R-value to be maintained or substantially maintained.

BACKGROUND AND SUMMARY OF EXAMPLE EMBODIMENTS OF THE INVENTION

The insulation of wall cavities is known in the art. For example, it is known to position insulating fiberglass batts in vertical wall cavities of a home or building in order to insulate the wall. Such insulation helps reduce the amount of heat which can escape a home or building to the outside in winter months for example. In addition to the use of fiberglass insulation, other types of insulation are also known such as cellulose insulation an foam insulation. These types of insulation have even been combined in certain instances.

It has been found by the instant inventors that the flow of air through fiberglass insulation has a significant detrimental effect on the R-value or thermal performance of the insulation, especially in cold weather conditions. In particular, it has been found that the flow of air through fiberglass can significantly decrease the effective R-value of the insulation in a vertical wall cavity or the like.

In certain example embodiments of this invention, a dynamic heat flow meter, and method, is/are provided for testing thermal properties of fiberglass inclusive insulation materials including apparent thermal conductivity and/or heat capacity. Thermal properties, such as thermal conductivity, are important physical properties of insulation or the like. Heat flows through insulation that has a temperature gradient across its volume. The thermal conductivity of a specimen can be measured directly by measuring the heat flux resulting from a known temperature gradient across a known thickness of the material.

Figure 1:
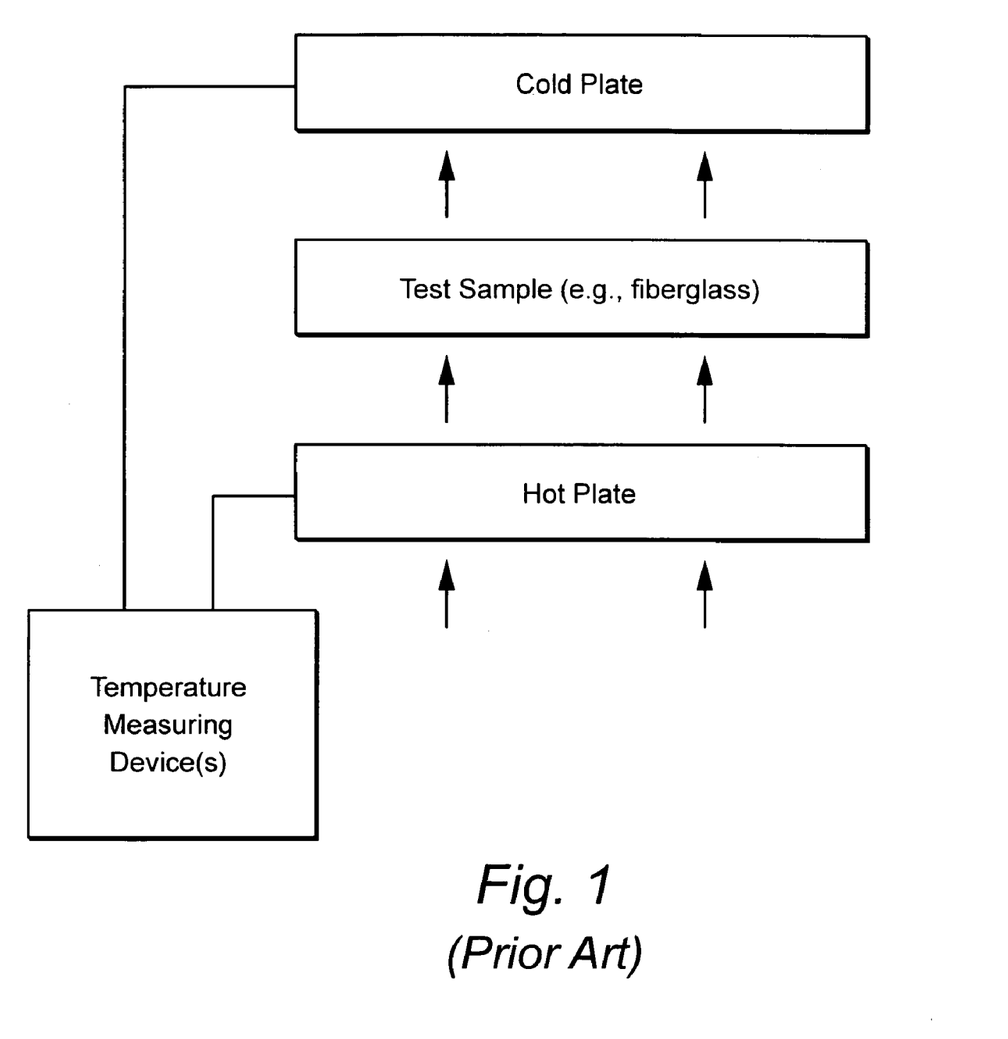
FIG. 1 is a schematic diagram of a conventional steady state or static heat flow meter, that does not take air flow into account.

A one-dimensional form of the Fourier heat flow relation is sometimes used to calculate thermal conductivity under steady-state conditions: $k=Q(\Delta X/\Delta T)$, where "k" is thermal conductivity, "Q" is a heat flow per a unit surface area (heat flux), and $\Delta T$ is a temperature difference over the thickness $\Delta X$. Prior Art FIG. 1 illustrates a conventional static heat flow meter for measuring the thermal conductivity of a test sample (e.g., piece of insulation such as fiberglass). The test sample or specimen is located between two flat plates, and the plates are maintained at known, but different, temperatures. As heat flows through the test sample from the hot side to the cold side, a heat flux transducer (not shown) measures the amount of heat transferred. Thermocouple(s) or other temperature measuring device(s) measure the temperatures of each of the two plates (i.e., of the so-called hot and cold plates). These values are then plugged into the above-listed equation, so that the thermal conductivity of the test sample or specimen can be calculated based on the measured values. Such measurements are often done in accordance with standard testing methods such ASTM C 518, which is incorporated herein by reference. It is in such a manner that insulation products such as fiberglass batts are assigned so-called "R-values"—based on their steady state or static measured thermal properties per ASTM C 518 (e.g., R11 fiberglass insulation batt, etc.).

Unfortunately, the standard testing device of FIG. 1 discussed above determines thermal properties of the test sample via steady state or static testing, where there is no air flow (i.e., there is zero air movement introduced into the testing equipment during the testing). Thus, measurements from such devices can be deceiving as will be explained below, because they do not measure the effects of air flow through the insulation.

When insulation (e.g., fiberglass insulation batt, fiberglass loose-fill, combination/laminate of fiberglass and foam insulation, or the like) is provided in a vertical wall cavity of a home (e.g., between two-by-four studs as is known in the art), it has been found that air flow (e.g., due to wind or the like in the environment surrounding or adjacent to the home) through the wall can have an adverse effect on insulation properties. Contributions to total building heating or cooling load include the change in enthalpy of air moving through an insulation (e.g., fiberglass) and the heat flux through the insulation due to the imposed thermal gradient. The two effects are not independent since the air movement affects the temperature distribution in the insulation. One may experience an example of air flow in an exterior wall of a home by feeling a cool draft in the winter when one puts his or her hand adjacent an electrical outlet. Such air flows in or through walls, or through fiberglass insulation, can reduce the thermal performance of insulation, since insulation such as fiberglass is not an air barrier as it does not stop air flow.

As explained above, unfortunately, the conventional heat flow meter shown in FIG. 1 and discussed above does not take air flow into account when measuring thermal properties of the test sample.

According to certain example embodiments of this invention, a heat flow meter, and/or method, is/are provided for measuring thermal properties of a product (e.g., insulation product) in a manner which takes into account dynamic air flow. For example, the effect of air flow through fiberglass insulation (e.g., a batt of fiberglass insulation) can be measured. In certain example embodiments, a heat flow meter is provided which introduces a measured air flow into the system adjacent the test sample (e.g., fiberglass insulation product) to be measured. The heat flow meter then measures thermal properties (e.g., thermal conductivity and/or heat capacity) of the insulation taking into account air flow through the test sample.

By taking into account intentionally introduced and measured air flow, temperature and/or moisture/humidity content of such air flow through and/or across the insulation (e.g., fiberglass insulation), one can determine how effective the particular sample would be in real-world conditions where wind (and thus air flow in/through home walls) is a frequent occurrence. This permits one to determine which types of insulation may be effective in certain types of environments.

This also permits one to determine the shortcomings of certain insulation products such as fiberglass batts in certain conditions such as cold weather conditions.

Once the disadvantages of the insulation product (e.g., fiberglass insulation batt or the like) are known via the dynamic heat flow meter which takes into account air flow through the insulation (e.g., once it is determined how much R-value is adversely affected by such air flow through the insulation), the overall insulation of a wall cavity or the like can be adapted to take these disadvantage(s) into account. For example, a sufficient amount of foam insulation may be provided in the vertical wall cavity so as to prevent or reduce air flow through the fiberglass, thereby compensating or substantially compensating for the adverse effects of air flow through the fiberglass and permitting the intended R-value(s) to be maintained or substantially maintained. In certain example instances, for purposes of example and without limitation, foam insulation having a thickness of from about one-quarter inch to three-quarters of an inch may be provided in a vertical wall cavity behind the fiberglass insulation in certain example instances, to reduce air flow through the fiberglass thereby compensating for the adverse effects of air flow through the fiberglass and permitting the intended R-value(s) to be maintained or substantially maintained. In other example embodiments, the foam insulation may be from about one quarter inch to about one and a half inches thick.

In certain example embodiments of this invention, there is provided a method of insulating a wall cavity, the method comprising: determining thermal properties of a fiberglass batt including effects of air flow through the fiberglass batt; and after determining the thermal properties of the fiberglass batt including the effects of air flow through the fiberglass batt, adapting an insulation system in a wall cavity to compensate, or substantially compensate, for the effects of air flow through the fiberglass batt by providing foam insulation in the wall cavity and then providing a fiberglass batt in the cavity over the foam insulation, wherein the foam insulation is of sufficient thickness and R-value to compensate, or substantially compensate, for the effects of air flow through the fiberglass batt.

In other example embodiments of this invention, there is provided a method of compensating for effects of air flow with respect to fiberglass insulation, the method comprising: determining or considering thermal properties of a fiberglass insulation product including effects of air flow on the fiberglass insulation; and based on at least the effects of air flow on the fiberglass insulation, providing an insulation system in a wall cavity in a manner so as to compensate, or substantially compensate, for the effects of air flow with respect to the fiberglass insulation by providing foam insulation in the wall cavity and then providing the fiberglass insulation in the cavity over the foam insulation, wherein the foam insulation is of sufficient thickness and R-value to compensate, or substantially compensate, for the effects of air flow through the fiberglass insulation.

In other example embodiments of this invention, there is provided a method of compensating for effects of air flow with respect to fibrous insulation such as fiberglass, cellulose or rock wool, the method comprising: determining or considering thermal properties of a fibrous insulation including effects of air flow on the fibrous insulation; and based on at least the effects of air flow on the fibrous insulation, providing an insulation system in a wall cavity in a manner so as to compensate, or substantially compensate, for the effects of air flow with respect to the fibrous insulation by providing foam insulation in the wall cavity and then providing the fibrous insulation in the cavity over the foam insulation, wherein the foam insulation is of sufficient thickness and R-value to compensate, or substantially compensate, for the effects of air flow through the fibrous insulation.

In still further example embodiments of this invention, there is provided an insulated wall cavity, comprising: a wall cavity; and foam insulation in the wall cavity and a fiberglass batt in the cavity over the foam insulation, wherein the foam insulation is of sufficient thickness and R-value to compensate, or substantially compensate, for the effects of air flow through the fiberglass batt.

DETAILED DESCRIPTION OF THE INVENTION

Referring now more particularly to the accompanying drawings in which like reference numerals indicate like parts throughout the several views.

Figure 7:
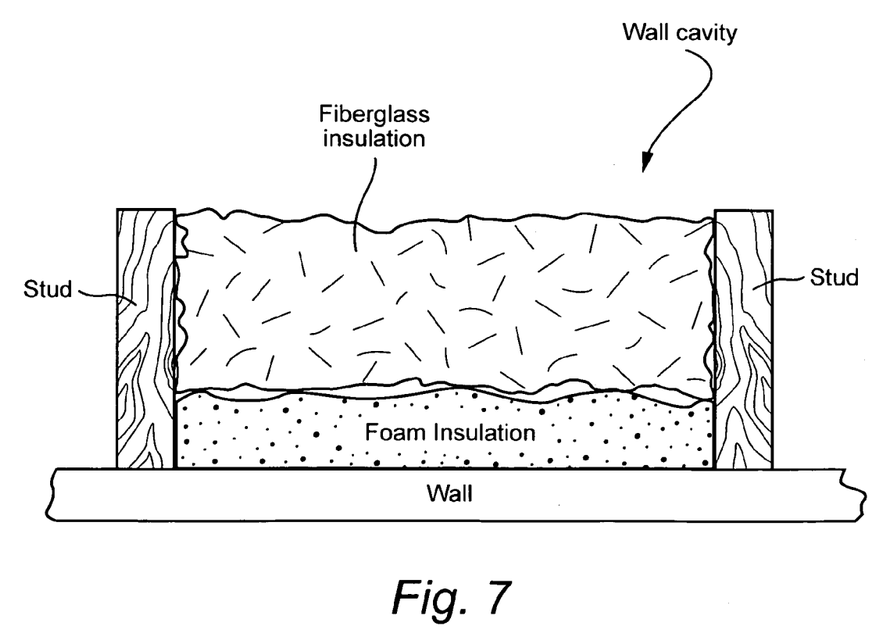
FIG. 7 is a cross sectional view of a wall cavity (vertical, slanted or horizontal) according to an example embodiment of this invention, where foam insulation is provided in the cavity behind the fiberglass insulation, the foam reducing air flow through the fiberglass thereby compensating for the adverse effects of air flow through the fiberglass and permitting the intended R-value(s) to be maintained or substantially maintained.

Certain example embodiments of this invention relate to a method and/or system that compensates for the flow of air through fiberglass insulation. In certain example embodiments, dynamic heat flow meter or the like is provided for measuring the thermal properties of a material (e.g., insulation such as fiberglass inclusive insulation, or any other suitable material) including determining any detrimental effects of air flow therethrough. Once the possible detrimental effects associated with air flow are recognized, the insulation system is adapted (e.g., by providing a foam based insulation in a wall cavity in addition to the fiberglass insulation) to compensate, or substantially compensate, for the effects of air flow through the fiberglass. For instance, a sufficient amount of foam insulation may be provided in the cavity adjacent the fiberglass insulation. In such a case, the foam insulation can prevent air flow and if provided behind the fiberglass can prevent (or reduce) air flow from reaching the fiberglass insulation. Thus, the foam can block or substantially block the air flow through the cavity, thereby compensating for the effects of air flow through fiberglass (e.g., by preventing air from flowing through the fiberglass, or by reducing the amount of air flowing through the fiberglass, or by blocking air that has already flowed through fiberglass from flowing through the entire cavity) and permitting the intended R-value to be maintained or substantially maintained. FIG. 7 is a cross sectional view of an example insulated wall cavity according to an example embodiment of this invention, where the foam is provided in the cavity behind the fiberglass. However, in alternative example embodiments, the foam may be provided over the fiberglass in the cavity so that the fiberglass is between the wall or back of the cavity and the foam insulation.

Figure 2:
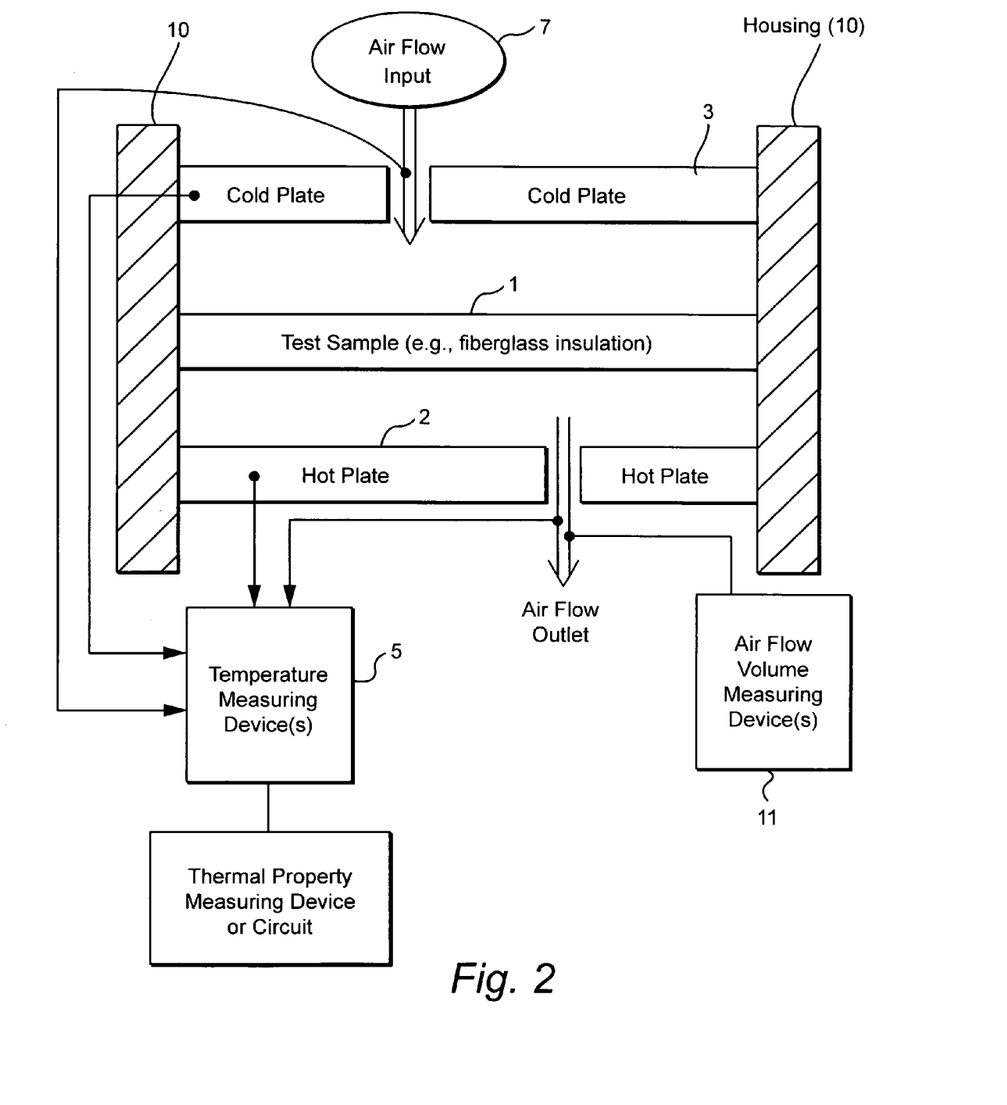
FIG. 2 is a schematic diagram of a dynamic heat flow meter according to an example embodiment of this invention.
Figure 3:
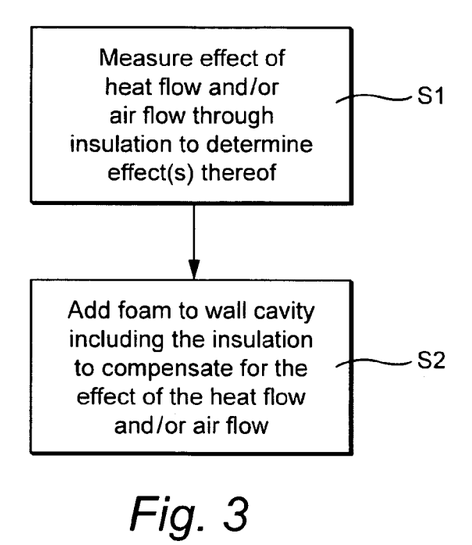
FIG. 3 is a flowchart illustrating steps performed according to an example embodiment of this invention.

FIG. 3 is a flowchart illustrating steps performed according to an example embodiment of this invention. In step S1, one measures or otherwise determines the possible detrimental effects of air flow through a material such as fiberglass insulation. This may be done using the dynamic heat flow meter described herein and shown in FIG. 2. For instance, it may be determined in step S1 that air flow through fiberglass can significantly reduce the R-value of the fiberglass or of the cavity in which the fiberglass is to be located (especially in cold weather conditions where the exterior of a home or building is much colder than the interior). Once one determines the detrimental effects of air flow on a particular type of insulation in S1, the insulation system is adapted in step S2 (e.g., by providing a foam based insulation in a wall cavity in addition to the fiberglass insulation) to compensate, or substantially compensate, for the effects of air flow through the fiberglass. For instance, as shown in FIG. 7, in step S2 a sufficient amount of foam insulation may be provided in the cavity adjacent the fiberglass insulation. In such a case, the foam insulation can prevent air flow and if provided behind the fiberglass as shown in FIG. 7 can prevent (or reduce) air flow from reaching the fiberglass insulation. Thus, the foam can block or substantially block the air flow through the wall cavity, thereby compensating for the effects of air flow through fiberglass.

FIG. 2 is a schematic diagram of a dynamic heat flow meter according to an example embodiment of this invention, that may be used in step S1 for example. The heat flow meter of FIG. 2 intentionally introduces a measured air flow adjacent the test sample (e.g., insulation product such as fiberglass insulation batt, loose-fill fiberglass insulation, loose-fill cellulose insulation, combination or laminate of fiberglass and foam insulation, etc.) to be measured. The air flow may be through and/or across the test sample. The heat flow meter then measures thermal properties (e.g., thermal conductivity and/or heat capacity) of the test sample taking into account air flow through the test sample. Moreover, the meter may also take into account the temperature and/or moisture/humidity content of such air flow across the insulation test sample. Because an intentionally introduced and measured air flow, which air flow at least partially proceeds through the test sample, is taken into account, one can determine how effective the particular sample (e.g., fiberglass insulation) would be in real-world conditions where wind (and thus air flow in/through home walls) is a frequent occurrence.

Still referring to FIG. 2, the test sample or specimen (1), such as fiberglass insulation, is located between two flat plates (2) and (3), and the plates are maintained at known, but different, temperatures. One plate (2) may be considered a hot plate, and the other (3) a cold plate since one is hotter than the other. As heat flows through the test sample (1) from the hot side to the cold side, it is possible for a heat flux transducer (not shown) to measure the amount of heat transferred. Thermocouple(s), thermistor(s), or other temperature measuring device(s) (5) measure the temperatures of each of the two plates (2 and 3). One or more aperture(s) may be provided in one of the plates (2 or 3) so as to allow a measured air flow from air flow input 7 to be introduced into a cavity of the measuring device and be directed toward and/or adjacent the test sample to be measured. The input air flow is measured (e.g., by volume). For example and without limitation, an example introduced air flow may be about 3 or 4 cubic feet per minute. The input air flow may be introduced either through an aperture(s) in the cold plate (3) as shown in FIG. 2, or alternatively through an aperture(s) in the hot plate (2) (i.e., it may be introduced from either side). At least part of, and preferably all of, the air flow that is introduced from input 7 through the aperture(s) in the plate flows through the test sample 1 and exits the heat flow meter via one or more aperture(s) in the other plate (e.g., see air flow output in FIG. 2).

Still referring to FIG. 2, the housing 10 surrounding the plates and test sample prevents any air flow from leaking out of the device, so that all or substantially all of the introduced air flow is forced to flow through the test sample 1. In certain example instances, a gasket(s) may be provided to improve the seal and make sure than air flow does not escape except through a designed air flow outlet(s). If the air flow volume measuring device 11 at the air flow outlet measures air flow at an amount more than a predetermined amount different than does an air flow volume measuring device (not shown) at the inlet proximate 7, then an alarm may be actuated to indicate that an air flow leak is present in this system.

Temperature measuring device(s) (5) measure the temperature of each of the hot plate, the cold plate, the input air flow, and the output air flow. Humidity may also be taken into account by the measure device(s). This information may be used in equation(s) in determining the thermal properties of the test sample.

FIG. 2 illustrates the measured air flow moving through the test sample, in a direction which is parallel to, or anti-parallel to, the heat-flow direction. The air is introduced into the cavity of the meter from an external temperature controlled source. The heat-flow meter with controlled air flow is used to determine total heat-flow rates as a function of air-flow rate, air flow direction, and temperature for commonly used wall cavity insulations for example. It is noted, however, that the direction of air flow in other embodiments may be in different directions.

The heat flow meter thus measures thermal properties (e.g., thermal conductivity and/or heat capacity) of the test sample taking into account air flow through the test sample. For example, if thermal conductivity can be measured as discussed above, with a known and measured air flow through and/or across the test sample 1, the products thermal properties can be determined as a function of air flow.

In certain example embodiments, the intentionally input measured air flow may be introduced into the cavity of the heat flow meter via an aperture(s) in housing 10, instead of an aperture(s) in one of the plates (2 or 3). Thus, in such embodiments, no aperture(s) in plate (3) is needed. It is also possible for the air flow outlet aperture(s) to be defined in housing 10 instead of in one of the plates (2 or 3), so long as the air flow inlet and air flow outlet are provided on opposite sides of the test sample 1. Thus, in certain example embodiments of this invention, there need not be any holes or aperture(s) in plate (2) and/or plate (3).

Figure 4:
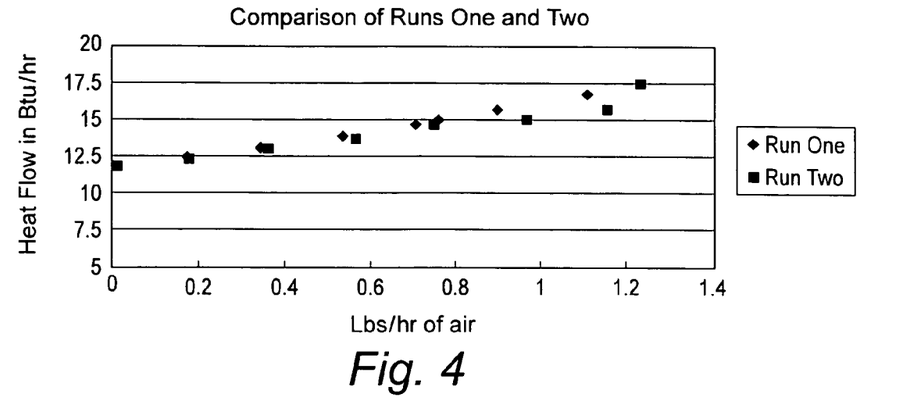
FIG. 4 is an air flow vs. heat flow graph according to certain tests performed according to example embodiments of this invention.
Figure 5:
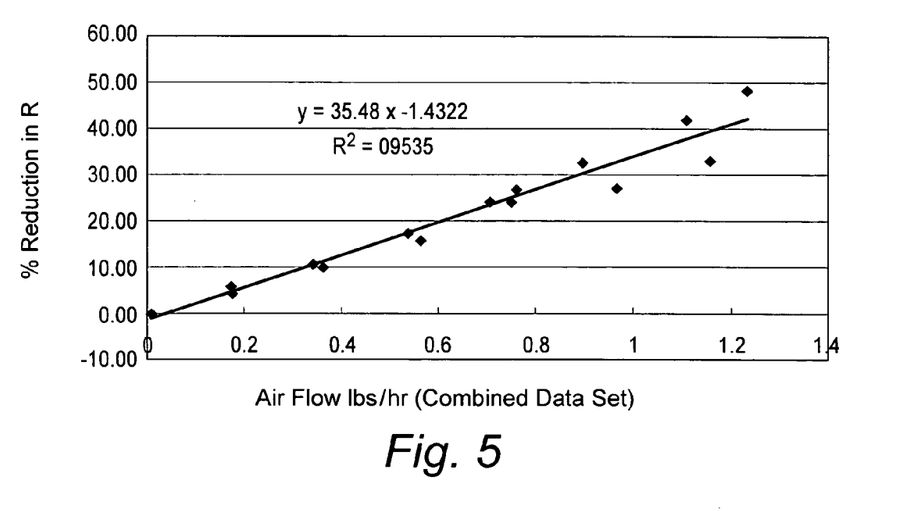
FIG. 5 is an air flow vs. percent reduction or decrease in effective R-value graph, illustrating the detrimental effects of air flow on fiberglass insulation according to example embodiments of this invention.
Figure 6:
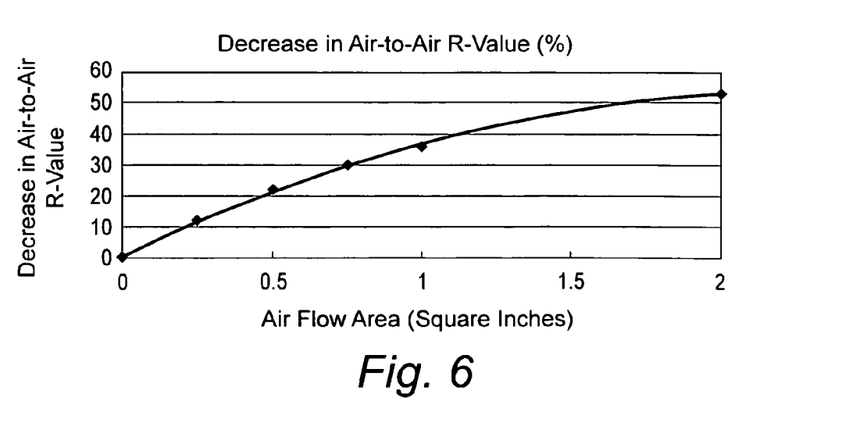
FIG. 6 is an air flow vs. decrease in air-to-air R-value according to an example embodiment of this invention, illustrating that increased air flow through fiberglass insulation reduces R-value thereof in cold exterior temperature conditions.

FIGS. 4-6 illustrate data taken with an example dynamic heat flow meter according to example embodiments of this invention (e.g., step S1 may include determination or measurement of data similar to that in one or more of FIGS. 4-6). The data in FIGS. 4-6 was obtained for a sequence of thermal measurements made using the FIG. 2 dynamic heat flow meter, which has the capability for moving air through a specimen during a thermal test. The air flow rate is measured and thermal instrumentation is provided to measure the hot and cold surfaces of the enclosure containing the specimen. The data or test results of FIGS. 4-6 were obtained for a nominal R11 fiberglass batt as the specimen in the meter. The air flow direction in the meter was opposite the heat flow direction, which would be the case in cold weather since the outside temperature is below indoor temperature and the heat flow direction is from the inside to the outside of the home or building.

FIG. 4 is an air flow vs. heat flow graph according to certain tests performed according to example embodiments of this invention. In particular, for the different indicated runs, the lbs./hr. of air flow can be translated into the illustrated heat flow in units of But/hr. FIG. 4 illustrates how heat flow into the cavity moves across the fiberglass batt and heats counter-flowing air, using a two foot by two foot R11 fiberglass batt in the FIG. 2 meter.

FIG. 5 is an air flow vs. percent reduction or decrease in effective R-value graph, illustrating the detrimental effects of air flow on fiberglass insulation according to example embodiments of this invention. Two different samples were measured at different air flows as shown in FIG. 5, with the same batt size and R-value as with FIG. 4. FIG. 5 illustrates that at 0 air flow, there is no decrease in R-value. However, as the air flow through the fiberglass batt increases (moving to the right in FIG. 5), the R-value of the batt decreases. This is because the heat flow in the cavity moves across the fiberglass batt and heats counter-flowing air, thereby decreasing the R-value in the cavity. Thus, FIG. 5 illustrates example detrimental effects of air flow through the fiberglass batt that is being tested in the meter. In particular, FIG. 5 illustrates that air flow through the insulation or cavity can cause the R-value of the insulation or cavity to decrease.

FIG. 6 is a general air flow area vs. decrease in air-to-air R-value according to an example embodiment of this invention, illustrating that increased air flow through fiberglass insulation reduces R-value thereof in cold exterior temperature conditions. The data from which the FIG. 6 graph was derived using the FIG. 2 dynamic heat flow meter was for an R19 Batt in a nominal 2×6 inch wood frame wall, for an outside temperature of about 20 degrees F and an inside temperature of about 70 degrees F, for sixty-four square feet of wall area. Again, it can be seen that air flow through the insulation or cavity causes the R-value of the insulation or cavity to decrease in cold weather conditions. In FIG. 6 for example, one square inch results in a calculated 39% reduction in air-to-air R-value.

Once the detrimental effects of air flow through a particular insulation product have been determined as in one or more of FIGS. 5 and/or 6, the insulation system is adapted (e.g., by providing a foam based insulation in a wall cavity in addition to the fiberglass insulation) to compensate, or substantially compensate, for the effects of air flow through the fiberglass batt. For instance, a sufficient amount of foam insulation may be provided in the cavity adjacent the fiberglass insulation. In such a case, the foam insulation can prevent air flow and if provided behind the fiberglass can prevent (or reduce) air flow from even reaching the fiberglass insulation. Thus, the foam can block or substantially block the air flow through the cavity, thereby compensating for the effects of air flow through fiberglass (e.g., by preventing air from flowing through the fiberglass, or by reducing the amount of air flowing through the fiberglass, or by blocking air that has already flowed through fiberglass from flowing through the entire cavity) and permitting the intended R-value to be maintained or substantially maintained.

FIG. 7 is a cross sectional view of an example insulated wall cavity according to an example embodiment of this invention, where the foam (e.g., closed cell polyurethane based foam) is provided in the cavity behind the fiberglass to compensate for the effects of air flow through fiberglass (e.g., this is an example of what may be done in step S2 of FIG. 3). Drywall (not shown) may be attached to the studs shown in FIG. 7 over the fiberglass insulation to seal the wall cavity. The wall cavity in FIG. 7 may be a vertical wall cavity, or any other type of wall cavity in different embodiments of this invention. In one example embodiment, the foam insulation may be about one-half inch thick and have about an R2-R3 R-value, and the overlying fiberglass insulation may be an R10, R11, R12, or R13 fiberglass batt which is from about 2.5 to 3.5 inches thick, more preferably about 3 inches thick (e.g., for standard 2 inch by 4 inch wood frame construction and corresponding cavities). In other example embodiments, R-3 foam (e.g., foam about one half-inch thick) may be used in combination with an R-16, R-19 or R-21 fiberglass batt about five inches thick (e.g., for 2 inch by 6 inch frame construction and corresponding cavities). In other example embodiments, R-3 foam (e.g., foam about one half-inch thick) may be used in combination with an R-21 or R-29 fiberglass batt about 6 and three-quarters inches thick (e.g., for 2 inch by 8 inch frame construction and corresponding cavities). In other example embodiments, R-3 foam (e.g., foam about one half-inch thick) may be used in combination with an R-30 fiberglass batt about eight and one-half inches thick (e.g., for 2 inch by 10 inch frame construction and corresponding cavities). In other example embodiments, R-3 foam (e.g., foam about one half-inch thick) may be used in combination with an R-38 fiberglass batt about ten and one-half inches thick (e.g., for 2 inch by 12 inch frame construction and corresponding cavities). Again, the foam may be closed-cell polyurethane, and may have an R-value of from about R2-R4, most preferably about R-3. This system increases thermal resistance and may virtually eliminate or reduce air infiltration thereby increasing energy efficiency.

In certain example embodiments, this invention permits the thermal performance of the insulation to be improved by at least about 10%, more preferably at least about 20%, even more preferably at least about 25%, and sometimes at least 30% by stopping or substantially stopping the air infiltration through the cavity.

It is noted that other types of fibrous insulation, such as cellulose or rock wool, may be used instead of fiberglass in certain alternative embodiments of this invention.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A method of insulating a wall cavity, the method comprising:
   determining thermal properties of a fiberglass batt including effects of air flow through the fiberglass batt using a dynamic heat flow meter, the dynamic heat flow meter comprising: housing defining at least one cavity therein; first and second plates at least partially provided in the housing, wherein the fiberglass batt is provided between the first and second plates; means for providing the first and second plates at known, but different, temperatures when the fiberglass batt is therebetween; means for introducing an air flow into the cavity of the meter on one side of the batt, and permitting air from the air flow to exit the cavity from the other side of the batt; and means for measuring properties of the batt using each of the air flow and temperatures of the respective first and second plates; and after determining the thermal properties of the fiberglass batt including the effects of air flow through the fiberglass batt, adapting an insulation system in a wall cavity to compensate, or substantially compensate, for the effects of air flow through the fiberglass batt by providing foam insulation in the wall cavity and then providing a fiberglass batt in the cavity over the foam insulation, wherein the foam insulation is of sufficient thickness and R-value to compensate, or substantially compensate, for the effects of air flow through the fiberglass batt.

2. The method of claim 1, wherein said compensating is performed by using the foam insulation to block air flow and/or wind from outside of a wall of the cavity from reaching the fiberglass batt.

3. The method of claim 1, wherein the first plate has an air flow inlet aperture(s) defined therein, and the second plate has an air flow outlet aperture(s) defined therein.

4. The method of claim 1, wherein the housing of the meter has an air flow inlet aperture(s) defined therein on a first side of the batt, and the housing further has an air flow outlet aperture(s) defined therein on a second side of the batt that is opposite the first side.

5. The method of claim 1, comprising measuring the volume of air flow both entering and exiting the cavity of the meter.

6. The method of claim 1, wherein the foam insulation is about one-half inch thick and has an R-value of about 2-4.

7. The method of claim 1, wherein the foam insulation has an R-value of about 3.

8. The method of claim 1, wherein the wall cavity is a two inch by four inch wood framed wall cavity, and the fiberglass batt has an R-value of from about R10 to R-13 and is about three inches thick, and the foam insulation is about one-half inch thick and has an R-value of about 2-4.

9. The method of claim 1, wherein the wall cavity is a two inch by eight inch wood framed wall cavity, and the fiberglass batt has an R-value of from about R21 to R-29 and is about 6-7 inches thick, and the foam insulation is about one-half inch thick and has an R-value of about 2-4.

10. A method of compensating for effects of air flow with respect to fibrous insulation, the method comprising:

determining or considering thermal properties of a fibrous insulation including effects of air flow on the fibrous insulation using a dynamic heat flow meter, the dynamic heat flow meter comprising: housing defining at least one cavity therein; first and second plates at least partially provided in the housing, wherein the fibrous insulation is provided between the first and second plates; means for providing the first and second plates at known, but different, temperatures when the fibrous insulation is therebetween; means for introducing an air flow into the cavity of the meter on one side of the insulation, and permitting air from the air flow to exit the cavity from the other side of the insulation; and means for measuring properties of the insulation using each of the air flow and temperatures of the respective first and second plates; and based on at least the effects of air flow on the fibrous insulation, providing an insulation system in a wall cavity in a manner so as to compensate, or substantially compensate, for the effects of air flow with respect to the fibrous insulation by providing foam insulation in the wall cavity and then providing the fibrous insulation in the cavity over the foam insulation, wherein the foam insulation is of sufficient thickness and R-value to compensate, or substantially compensate, for the effects of air flow through the fibrous insulation.

11. The method of claim 10, wherein the foam insulation blocks air flow and/or wind from outside of a wall of the cavity from reaching the fibrous insulation.

12. The method of claim 10, wherein the fibrous insulation is selected from the group consisting of fiberglass insulation, cellulose insulation, and rock wool insulation.

* * * * *